United States Patent
Suyama et al.

(10) Patent No.: US 10,267,751 B2
(45) Date of Patent: Apr. 23, 2019

(54) IMAGE ACQUISITION DEVICE AND IMAGE ACQUISITION METHOD

(71) Applicant: HAMAMATSU PHOTONICS K.K., Hamamatsu-shi, Shizuoka (JP)

(72) Inventors: Toshiyasu Suyama, Hamamatsu (JP); Tatsuya Onishi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 106 days.

(21) Appl. No.: 15/305,148

(22) PCT Filed: Feb. 2, 2015

(86) PCT No.: PCT/JP2015/052875
§ 371 (c)(1),
(2) Date: Oct. 19, 2016

(87) PCT Pub. No.: WO2015/162963
PCT Pub. Date: Oct. 29, 2015

(65) Prior Publication Data
US 2017/0038314 A1 Feb. 9, 2017

(30) Foreign Application Priority Data

Apr. 23, 2014 (JP) ................. 2014-089350

(51) Int. Cl.
*G01N 23/04* (2018.01)
*G01T 1/20* (2006.01)
*G01T 1/208* (2006.01)

(52) U.S. Cl.
CPC ............. *G01N 23/04* (2013.01); *G01T 1/208* (2013.01); *G01T 1/2018* (2013.01)

(58) Field of Classification Search
None
See application file for complete search history.

(56) References Cited

U.S. PATENT DOCUMENTS

| 4,736,401 | A | 4/1988 | Donges et al. |
| 6,163,029 | A | 12/2000 | Yamada et al. |

(Continued)

FOREIGN PATENT DOCUMENTS

| CN | 85107860 | 10/1986 |
| CN | 1530074 | 9/2004 |

(Continued)

OTHER PUBLICATIONS

International Preliminary Report on Patentability dated Nov. 3, 2016 for PCT/JP2015/052875.

*Primary Examiner* — Hoon K Song
(74) *Attorney, Agent, or Firm* — Drinker Biddle & Reath LLP (57) ABSTRACT

An image acquisition device is an image acquisition device that acquires an X-ray transmission image of an object conveyed in a conveyance direction, and the image acquisition device includes an X-ray irradiator that outputs an X-ray, a belt conveyor that conveys the object in the conveyance direction, an X-ray detection camera having a scintillator that converts an X-ray penetrating the object into scintillation light, a line scan camera that detects the scintillation light and outputs a detection signal, and an amplifier that amplifies the detection signal at a predetermined set amplification factor and outputs a amplified signal, a controller that generates an X-ray transmission image based on the amplified signal, and an amplifier controller that sets one of a first amplification factor or a second amplification factor corresponding to an amplification factor lower than the first amplification factor as the set amplification factor based on a predetermined imaging condition.

24 Claims, 5 Drawing Sheets

(56) References Cited

U.S. PATENT DOCUMENTS

| | | | |
|---|---|---|---|
| 2005/0047546 A1* | 3/2005 | Fox | H04N 5/32 378/91 |
| 2010/0119038 A1 | 5/2010 | Suyama et al. | |
| 2010/0119040 A1 | 5/2010 | Suyama et al. | |
| 2012/0145910 A1 | 6/2012 | Suyama | |
| 2013/0256542 A1 | 10/2013 | Soh et al. | |

FOREIGN PATENT DOCUMENTS

| | | |
|---|---|---|
| CN | 1936555 | 3/2007 |
| CN | 101266217 | 9/2008 |
| CN | 102192918 | 9/2011 |
| CN | 103168252 | 6/2013 |
| JP | H10-185841 A | 7/1998 |
| JP | H11-94532 A | 4/1999 |
| JP | 2006-319414 A | 11/2006 |
| JP | 2009-080028 A | 4/2009 |
| JP | 2009-085627 | 4/2009 |
| JP | 2014-033813 A | 2/2014 |
| JP | 2014-059209 A | 4/2014 |

* cited by examiner

IMAGE ACQUISITION DEVICE AND IMAGE ACQUISITION METHOD

TECHNICAL FIELD

An aspect of the present invention relates to an image acquisition device and an image acquisition method of acquiring a radiation image of an object.

BACKGROUND ART

There is a known image acquisition device that acquires a radiation image which is a radiation transmission image of an object carried on a belt conveyor for the purpose of a contamination inspection (for example, see Patent Literature 1). In such an image acquisition device, a radiation image of a conveyed object is acquired using a line scan camera.

CITATION LIST

Patent Literature

Patent Literature 1: Japanese Unexamined Patent Publication No. 2009-080028

SUMMARY OF INVENTION

Technical Problem

The above-described technology using a radiation image is an effective technology in conducting a contamination inspection. However, a further improvement in definition of an acquired radiation image is required. In this regard, an object of an aspect of the invention is to provide an image acquisition device and an image acquisition method capable of acquiring a clearer radiation image.

Solution to Problem

An image acquisition device according to an aspect of the invention is a device that acquires a radiation image of an object conveyed in a conveyance direction, the image acquisition device including a radiation source that outputs radiation, a carrier device that conveys the object in the conveyance direction, a detector having a scintillator that converts radiation penetrating the object into scintillation light, a line scan camera that detects the scintillation light and outputs a detection signal, and an amplifier that amplifies the detection signal at a predetermined set amplification factor and outputs a amplified signal, an image generator that generates a radiation image based on the amplified signal, and a setting unit that sets one of a first amplification factor or a second amplification factor corresponding to an amplification factor lower than the first amplification factor as the set amplification factor based on a predetermined imaging condition.

In addition, an image acquisition device according to an aspect of the invention is a device that acquires a radiation image of an object conveyed in a conveyance direction, the image acquisition device including a radiation source that outputs radiation, a carrier device that conveys the object in the conveyance direction, a detector having a scintillator that converts radiation penetrating the object into scintillation light, a line scan camera that detects the scintillation light and outputs a detection signal, and an amplifier that amplifies the detection signal at an amplification factor set based on a predetermined imaging condition and outputs a amplified signal, and an image generator that generates a radiation image based on the amplified signal.

Further, an image acquisition method according to an aspect of the invention is a method of acquiring a radiation image of an object conveyed in a conveyance direction, the image acquisition method including a step of converting radiation penetrating the object into scintillation light, detecting the scintillation light using a line scan camera, and outputting a detection signal, a step of setting one of a first amplification factor or a second amplification factor corresponding to an amplification factor lower than the first amplification factor as a set amplification factor based on a predetermined imaging condition, a step of amplifying the detection signal at the set amplification factor and outputting a amplified signal, and a step of generating a radiation image based on the amplified signal.

In addition, an image acquisition method according to an aspect of the invention includes respective steps of detecting radiation penetrating an object using a line scan camera while conveying the object in a conveyance direction, outputting a detection signal, amplifying the detection signal at an amplification factor based on a predetermined imaging condition and outputting a amplified signal, and generating a radiation image based on the amplified signal.

In the image acquisition device and the image acquisition method, a detection signal based on radiation penetrating an object is amplified at a predetermined set amplification factor, and a radiation image is generated. In addition, the set amplification factor is set based on a predetermined imaging condition. For example, one of a first amplification factor or a second amplification factor corresponding to an amplification factor lower than the first amplification factor is set. An amplification factor suitable to generate a clear radiation image is changed according to imaging condition. Thus, a clear radiation image may be generated when the set amplification factor is set according to imaging condition.

In addition, in an image acquisition device and an image acquisition method according to an aspect of the invention, the line scan camera may have a plurality of line sensors arranged in a line in a direction intersecting the conveyance direction. In this way, scintillation light pertaining to the object conveyed in the conveyance direction may be reliably detected using the plurality of line sensors arranged, in the line in the direction intersecting the conveyance direction.

In addition, in an image acquisition device and an image acquisition method according to an aspect of the invention, an imaging condition may be a parameter pertaining to luminance values of a plurality of pixels of a radiation image. A set amplification factor may be appropriately set when the luminance values of the pixels are set as an imaging condition.

In addition, in an image acquisition device and an image acquisition method according to an aspect of the invention, an imaging condition may be set based on a radiation image which is generated by the image generator. The imaging condition may be reliably and easily set when the imaging condition is set based on the radiation image which is generated by the image generator.

In addition, in an image acquisition device and an image acquisition method according to an aspect of the invention, an imaging condition may be set based on a radiation image which is generated by the image generator under a circumstance in which the set amplification factor is set to the first amplification factor. A parameter pertaining to a luminance value of a pixel is easily specified in a radiation image generated at the first amplification factor which is a relatively high amplification factor. For this reason, an imaging condition may be appropriately set based on the radiation image.

In addition, in an image acquisition device and an image acquisition method according to an aspect of the invention, a parameter pertaining to a luminance value may be a statistical value of luminance values of a plurality of pixels of a radiation image. In this way, a set amplification factor may be more appropriately set.

In addition, in an image acquisition device and an image acquisition method according to an aspect of the invention, the statistical value may be a variation degree of luminance values of a plurality of pixels. A set amplification factor may be appropriately set when the variation degree is considered.

In addition, in an image acquisition device and an image acquisition method according to an aspect of the invention, a plurality of pixels of a radiation image may be a plurality of pixels pertaining to different spaces of the radiation image. In this way, a set amplification factor may be appropriately set in consideration of a parameter of the plurality of pixels pertaining to the different spaces of the radiation image.

In addition, in an image acquisition device and an image acquisition method according to an aspect of the invention, a plurality of pixels of a radiation image may be a plurality of pixels pertaining to different times of the radiation image. In this way, a set amplification factor may be appropriately set in consideration of a parameter of the plurality of pixels pertaining to the different times of the radiation image.

In addition, in an image acquisition device and an image acquisition method according to an aspect of the invention, an imaging condition may be an output parameter of the radiation source. A set amplification factor may be appropriately set when the output parameter of the radiation source is set as the imaging condition.

In addition, in an image acquisition device according to an aspect of the invention, the setting unit may have a table corresponding to a parameter which is an imaging condition, and a set amplification factor may be set using the table. In addition, in an image acquisition method according to an aspect of the invention, in a step of setting a set multiplication factor, the set amplification factor may be set using a table corresponding to a parameter which is an imaging condition. A set amplification factor may be reliably and easily set when the amplification factor is set using the table.

In addition, in an image acquisition device according to an aspect of the invention, the setting unit may have a threshold value corresponding to a parameter which is an imaging condition, and a set amplification factor may be set using the threshold value. In addition, in an image acquisition method according to an aspect of the invention, in a step of setting a set multiplication factor, the set amplification factor may be set using a threshold value corresponding to a parameter which is an imaging condition. A set amplification factor may be reliably and easily set when the amplification factor is set using the threshold value.

Advantageous Effects of Invention

According to an aspect of the invention, it is possible to acquire a clear radiation image.

DESCRIPTION OF EMBODIMENTS

Hereinafter, a description will be given of an image acquisition device and an image acquisition method using the image acquisition device according to the present embodiment with reference to drawings. The same reference numeral will indicate the same or corresponding portion in description of the drawings, and a repeated description will be omitted.

Figure 1:
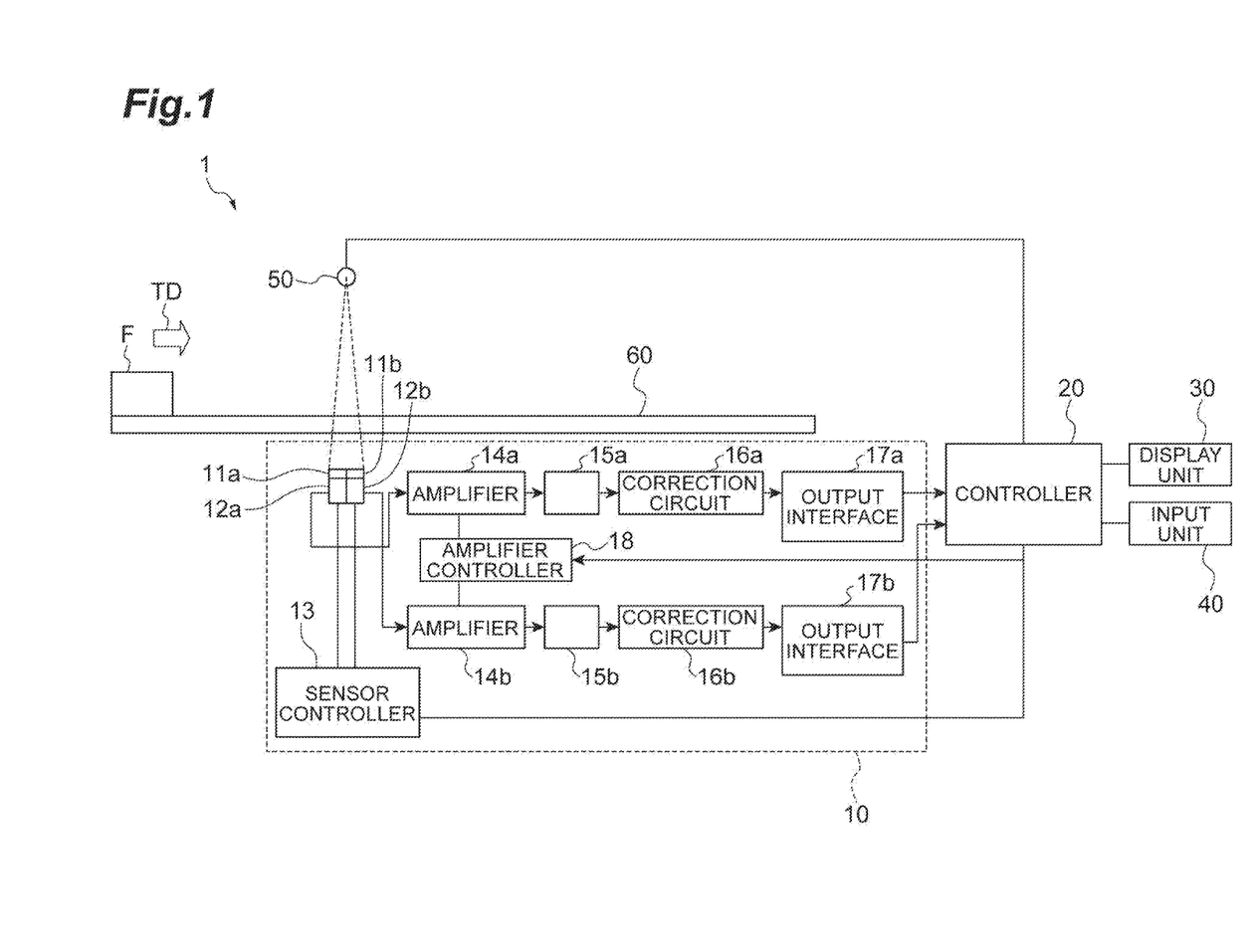
FIG. 1 is a block diagram of an image acquisition device according to the present embodiment.

FIG. 1 is a block diagram of an image acquisition device 1 according to the present embodiment. As illustrated in FIG. 1, the image acquisition device 1 is a device that irradiates an object F conveyed in a conveyance direction TD with an X-ray, and acquires an X-ray transmission image corresponding to a radiation image based on the X-ray penetrating the object F. The image acquisition device 1 detects a foreign material contained in the object F or conducts a baggage inspection, a substrate inspection, or the like using the X-ray transmission image. The image acquisition device 1 includes a belt conveyor 60 corresponding to a carrier device, an X-ray irradiator 50 corresponding to a radiation source, an X-ray detection camera 10, a controller 20 corresponding to an image generator, a display unit 30, and an input unit 40 for performing various inputs.

The belt conveyor 60 includes a belt portion on which the object F is placed, and conveys the object F at a predetermined conveyance speed in the conveyance direction TD by moving the belt portion in the conveyance direction TD. For example, the conveyance speed of the object F is 48 m/min. For example, the belt conveyor 60 may change the conveyance speed to a conveyance speed such as 24 m/min, 96 m/min, as necessary. In addition, the belt conveyor 60 may appropriately change a height position of the belt portion to change a distance between the X-ray irradiator 50 and the object F. Examples of the object F conveyed by the belt conveyor 60 may include various articles such as food such as meat, a rubber product such as a tire, a resin product, a metal product, a resource material such as a mineral, a waste material, an electronic component, and an electronic substrate.

The X-ray irradiator 50 is a device serving as an X-ray source which irradiates the object F with an X-ray. The X-ray irradiator 50 is a point light source, and performs irradiation by diffusing an X-ray in a fixed irradiation direction in a predetermined angle range. The X-ray irradiator 50 is disposed a predetermined distance away from the belt conveyor 60 above the belt conveyor 60 such that the irradiation direction of the X-ray is directed to the belt conveyor 60, and the diffused X-ray reaches the whole object F in a width direction thereof; that is, a direction intersecting the conveyance direction TD. In addition, in a length direction of the object F, that is, in a direction parallel to the conveyance direction TD, a predetermined divided range in the length direction is regarded as an irradiation range of the X-ray irradiator 50. Further, when the object F is conveyed in the conveyance direction TD by the belt conveyor 60, the whole object F in the length direction is irradiated with the X-ray. A tube voltage and a tube current are set by the controller 20, and the X-ray irradiator 50 irradiates the belt conveyor 60 with an X-ray having predetermined energy and radiation quantity corresponding to the set tube voltage and tube current.

The X-ray detection camera 10 detects an X-ray penetrating the object F in an X-ray with which the object F is irradiated by the X-ray irradiator 50, and outputs a signal based on the X-ray. The X-ray detection camera 10 is a dual-line X-ray camera in which two sets of configurations for detecting an X-ray are disposed. In the image acquisition device 1 according to the present embodiment, respective X-ray transmission images are generated based on X-rays detected in a first line and a second line corresponding to respective lines of the dual-line X-ray camera. In addition, if averaging processing or addition processing is performed on the two generated X-ray transmission images, a clear image, that is, an image having high luminance may be acquired at a small amount of X-ray when compared to a case in which an X-ray transmission image is generated based on an X-ray detected in one line.

The X-ray detection camera 10 includes scintillators 11a and 11b, line scan cameras 12a and 12b, a sensor controller 13, amplifiers 14a and 14b, A-D converters 15a and 15b, correction circuits 16a and 16b, output interfaces 17a and 17b, and an amplifier controller 18 corresponding to a setting unit. The scintillator 11a, the line scan camera 12a, the amplifier 14a, the A-D converter 15a, the correction circuit 16a, and the output interface 17a are electrically connected to one another, and correspond to a configuration pertaining to the first line. In addition, the scintillator 11b, the line scan camera 12b, the amplifier 14b, the A-D converter 15b, the correction circuit 16b, and the output interface 17b are electrically connected to one another, and correspond to a configuration pertaining to the second line. The line scan camera 12a of the first line and the line scan camera 12b of the second line are disposed side by side along the conveyance direction TD. Hereinafter, with regard to a configuration common to the first line and the second line, the configuration of the first line will be representatively described.

The scintillators 11a is fixed onto the line scan camera 12a by adhesion, or the like and converts an X-ray penetrating the object F into scintillation light. The scintillator 11a outputs the scintillation light to the line scan camera 12a.

The line scan camera 12a detects the scintillation light from the scintillators 11a, converts the scintillation light into an electric charge, and outputs the converted electric charge as a detection signal to the amplifier 14a. The line scan camera 12a includes a plurality of line sensors arranged in a line in a direction intersecting the conveyance direction TD. For example, the line sensors correspond to a charge coupled device (CCD) image sensor, or a complementary metal-oxide semiconductor (CMOS) image sensor, and have a plurality of photodiodes.

The sensor controller 13 controls the line scan cameras 12a and 12b to repeatedly capture images at a predetermined detection period such that the line scan cameras 12a and 12b may capture images of X-rays penetrating the same region of the object F. For example, a period common to the line scan cameras 12a and 12b may be set as the predetermined detection period based on a distance between the line scan cameras 12a and 12b, a speed of the belt conveyor 60, a focus object distance (FOD) corresponding to a distance between the X-ray irradiator 50 and the object F on the belt conveyor 60, and a focus detector distance (FDD) corresponding to a distance between the X-ray irradiator 50 and the line scan cameras 12a and 12b. Alternatively, respective predetermined periods may be individually set based on pixel widths of photodiodes in directions perpendicular to directions in which pixels of the line sensors of the respective line scan cameras 12a and 12b are arranged. In this case, a shift in detection period between the line scan cameras 12a and 12b, that is, a delay time may be specified depending on the distance between the line scan cameras 12a and 12b, the speed of the belt conveyor 60, the FOD corresponding to the distance between the X-ray irradiator 50 and the object F on the belt conveyor 60, and the FDD corresponding to the distance between the X-ray irradiator 50 and the line scan cameras 12a and 12b, and respective individual periods may be set.

The amplifier 14a amplifies the detection signal at a predetermined set amplification factor, and outputs the amplified signal to the A-D converter 15a. The set amplification factor is an amplification factor set by the amplifier controller 18. The amplifier controller 18 sets the set amplification factor of the amplifiers 14a and 14b to one of high gain corresponding to a relatively high amplification factor or low gain corresponding to a lower amplification factor than the high gain based on a predetermined imaging condition. Gain conversion is performed by changing a capacitance. For example, it is possible to select from 30 types at 0.5 pF intervals from 0.5 pF to 15 pF. Low gain may be a relatively lower amplification factor than high gain. For example, when 15 pF corresponding to a maximum value is set to one time, low gain is an amplification factor corresponding to one time, and high gain is twice the amplification factor. Capacitances may be freely combined, the number of capacitances may correspond to any number of types, and a range of low gain and high gain may be freely set.

Figure 2:
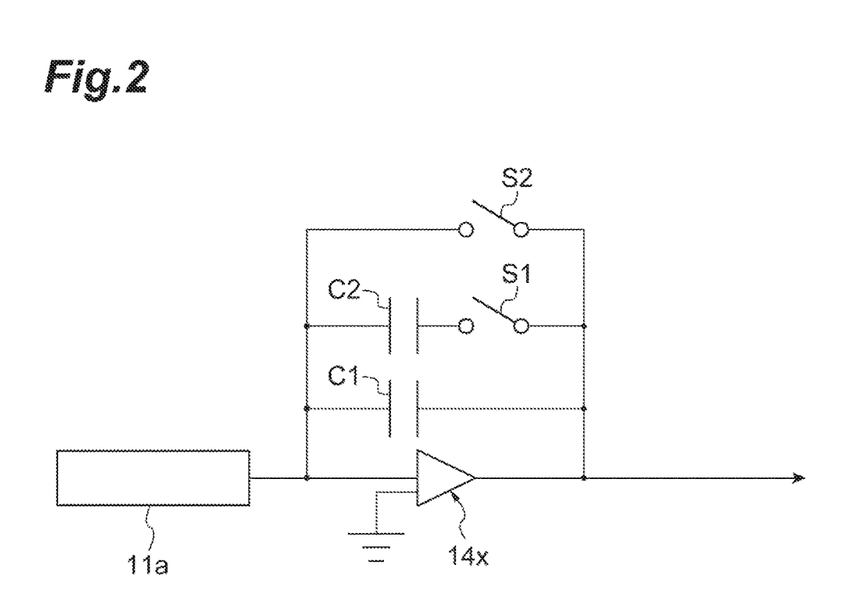
FIG. 2 is a diagram for description of an example of a current-voltage converting amplifier.
Figure 3:
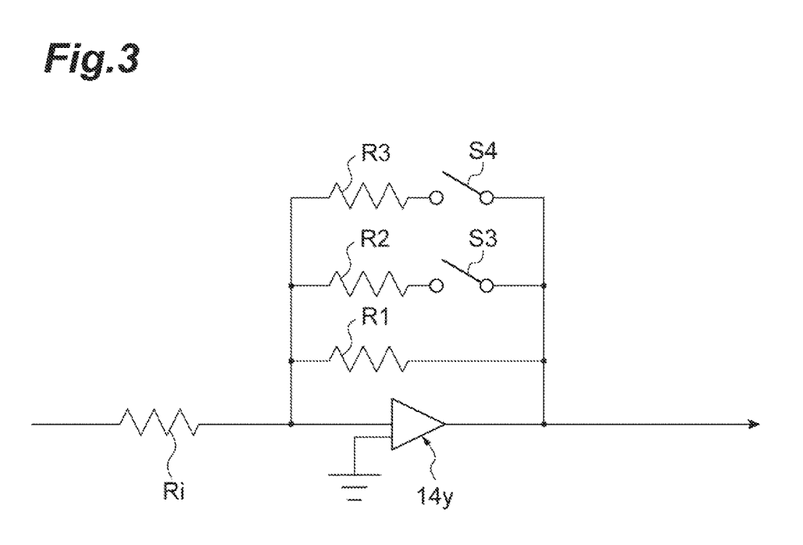
FIG. 3 is a diagram for description of an example of a voltage amplifier.

For example, as illustrated in FIG. 2 and FIG. 3, at least one of a current-voltage converting amplifier 14x that amplifies a current signal and a voltage amplifier 14y that amplifies a voltage signal may be used as the amplifier 14a. With regard to each of a case in which the amplifier 14a includes the current-voltage converting amplifier 14x and a case in which the amplifier 14a includes the current-voltage converting amplifier 14x and the voltage amplifier 14y, setting of the set amplification factor by the amplifier controller 18 will be described in detail with reference to FIG. 2 and FIG. 3. An example illustrated in FIG. 2 is an example in which capacitances are connected in parallel to the current-voltage converting amplifier 14x, and an example illustrated in FIG. 3 is an example in which feedback resistors are connected in parallel to the voltage amplifier 14y.

In the example illustrated in FIG. 2, the current-voltage converting amplifier 14x coverts a current signal output from a photodiode of the line scan camera 12a into a voltage signal. A capacitance C1 is connected in parallel to the current-voltage converting amplifier 14x. In this way, the current signal is amplified at an amplification factor according to the capacitance C1, for example, the above-described second amplification factor, and is output as a voltage signal. Further, a capacitance C2 is connected in parallel to the current-voltage converting amplifier 14x through a switch S1. When the switch S1 is in a connected state, that is, a closed state, the current signal is amplified at an amplification factor according to a total capacitance of the capacitance C1 and the capacitance C2 which is greater than an amplification factor corresponding to a case of only the capacitance C1, for example, the above-described first amplification factor, and is output as a voltage signal. Further, a switch S2 is connected in parallel to the current-voltage converting amplifier 14x. The switch S2 is a switch for resetting a capacitance. The amplifier controller 18 sets a set amplification factor of the current-voltage converting amplifier 14x by controlling opening and closing of the switch S1 and the switch S2. The capacitances C1 and C2 may be the same capacitance, or may be different from each other. In addition, the number of capacitances is not restricted to two, and three or more capacitances may be used.

Further, in the example illustrated in FIG. 3, the voltage amplifier 14y amplifies the voltage signal output from the current-voltage converting amplifier 14x. Respective feedback resistors R1, R2, and R3 are connected in parallel to the voltage amplifier 14y. The feedback resistor R2 is connected in parallel through a switch S3, and the feedback resistor R3 is connected in parallel through a switch S4. Herein, a set amplification factor is determined based on a ratio of a resistance value of an input resistor Ri provided on an input side to resistance values of the feedback resistors. The amplifier controller 18 changes resistance values of the feedback resistors by controlling opening and closing of the switch S3 and the switch S4, and sets a set amplification factor of the voltage amplifier 14y. Resistance values of the feedback resistors R1, R2, and R3 may be the same or may be different from one another. In addition, the set amplification factor may be set from more amplification factors by increasing the number of feedback resistors.

Returning to FIG. 1, the A-D converter 15a converts the amplified signal output from the amplifier 14a into a digital signal, and outputs the converted signal to the correction circuit 16a. The correction circuit 16a performs a predetermined correction such as signal amplification on the digital signal, and outputs the corrected digital signal to the output interface 17a. The output interface 17a outputs the digital signal to the outside of the X-ray detection camera 10.

Examples of the controller 20 include a computer such as a personal computer (PC). The controller 20 generates an X-ray transmission image based on digital signals output from the X-ray detection camera 10, more specifically, the output interfaces 17a and 17b. The controller 20 generates one X-ray transmission image by performing averaging processing or addition processing on two digital signals output from the output interfaces 17a and 17b. The generated X-ray transmission image is output to the display unit 30, and is displayed by the display unit 30. In addition, the controller 20 controls the X-ray irradiator 50 and the sensor controller 13.

Further, the controller 20 specifies a predetermined imaging condition, and outputs the specified imaging condition to the amplifier controller 18. The predetermined imaging condition is a setting criterion for setting set amplification factors for the amplifiers 14a and 14b by the amplifier controller 18. The controller 20 specifies the imaging condition according to a signal region of an X-ray emitted from the X-ray irradiator 50. Any one of $Gd_2O_2S$:Tb, $Gd_2O_2S$:Pr, CsI:Tl, $CdWO_4$, $CaWO_4$, $Gd_2SiO_5$:Ce, $Lu_{0.4}Gd_{1.6}SiO_5$, $Bi_4Ge_3O_{12}$, $Lu_2SiO_5$:Ce, $Y_2SIO_5$, $YALO_3$:Ce, $Y_2O_2S$:Tb, or $YTaO_4$:Tm may be used for the scintillators 11a and 11b. Fluorescence conversion efficiency varies according to a type of scintillator, and it is desirable to be able to set an amplification factor of an amplifier according to the fluorescence conversion efficiency. For example, it is presumed that the controller 20 uses $CdWO_4$ for a scintillator unit. In general, $CdWO_4$ has a fluorescence conversion quantity of about 12 to 15 [photon/keV], and a fluorescence conversion quantity of X-ray photons of $CdWO_4$ is lower than that of CsI(Tl): about 54 [photon/keV] or GOS(Tb): about 60 [photon/keV]. In addition, under the condition that X-ray energy is low, for example, at a tube voltage of 30 kV, a quantity of conversion of X-ray photons into visible light further decreases.

A description will be given using an example of a case in which low gain is set to one time, high gain is set to two times, and 12-bit output is set under the condition that a conversion quantity is low when X-ray photons are converted into visible light as described above, that is, under the condition that the scintillator unit is $CdWO_4$ having a low fluorescence conversion quantity, and a tube voltage is set to 30 kV. In this condition, for example, when a signal region is smaller than 300 counts in a region in which circuit-based noise is more dominant than quantum noise as noise components of an image, "signal region is smaller than 300 counts" is set as the imaging condition. The amplifier controller 18 sets a set amplification factor to high gain based on the imaging condition corresponding to "signal region is smaller than 300 counts". In addition, since high gain is presumed to be two times, the controller 20 cannot apply gain to a value greater than 2047 counts corresponding to half a maximum value of 4095 counts of the 12-bit output. Thus, when a signal region is larger than 2047 counts, "signal region is larger than 2047 counts" is set as the imaging condition. The amplifier controller 18 sets a set amplification factor to low gain based on the imaging condition corresponding to "signal region is larger than 2047 counts". Herein, when a signal region is larger than or equal to 300 counts and smaller than or equal to 2047 counts, the controller 20 sets an output parameter of the X-ray irradiator 50 or a parameter pertaining to luminance values of a plurality of pixels of the X-ray transmission image as the imaging condition. Hereinafter, a description will be given of specifying an imaging condition when a signal region is larger than or equal to 300 counts and smaller than or equal to 2047 counts. This set value varies according to a gain magnification or a type of scintillator, and thus a set value may be changed according to each condition.

The controller 20 set an output parameter of the X-ray irradiator 50, specifically a tube voltage and a tube current pertaining to an X-ray output from the X-ray irradiator 50, as an imaging condition. When the tube voltage pertaining to the X-ray set as the imaging condition by the controller 20 is higher than a predetermined value, and the tube current pertaining to the X-ray set as the imaging condition by the controller 20 is lower than a predetermined value, the amplifier controller 18 sets a set amplification factor to low gain based on the imaging condition. On the other hand, when the tube voltage pertaining to the X-ray set as the imaging condition by the controller 20 is lower than the predetermined value, and the tube current pertaining to the X-ray set as the imaging condition by the controller 20 is higher than the predetermined value, the amplifier controller 18 sets a set amplification factor to high gain based on the imaging condition.

In addition, the controller 20 sets a parameter pertaining to luminance values of a plurality of pixels of the X-ray transmission image as an imaging condition. The imaging condition based on the parameter pertaining to the luminance values is specified based on the X-ray transmission image generated by the controller 20. The imaging condition may be specified based on an X-ray transmission image generated by image capturing in a state in which the object F is not conveyed, or may be specified based on an X-ray transmission image generated by image capturing in a state in which a test piece is conveyed. Further, the imaging condition may be specified based on an X-ray transmission image generated by the controller 20 in an environment in which a set amplification factor is set to high gain. Hereinafter, a description will be given of specifying an imaging condition based on an X-ray transmission image with reference to FIG. 4.

Figure 4:
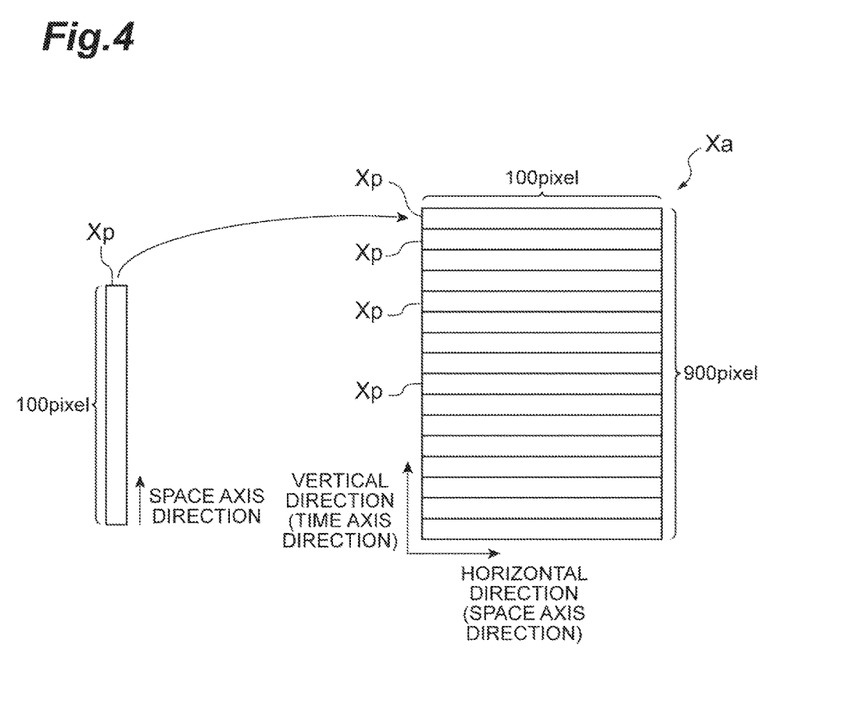
FIG. 4 is a diagram for description of setting of an imaging condition based on an X-ray transmission image.

For example, a parameter pertaining to luminance values of a plurality of pixels of an X-ray transmission image is specified based on an X-ray transmission image Xa obtained by combining a plurality of X-ray transmission images Xp, each of which is acquired by performing image capturing once (see FIG. 4). In an example illustrated in FIG. 4, an X-ray transmission image Xp acquired by performing image capturing once includes a plurality of pixels corresponding to 100 pixels which is the number of pixels of a line sensor. Such a plurality of pixels is a plurality of pixels pertaining to different spaces of an X-ray transmission image. Hereinafter, a description may be given on the assumption that a space axis direction corresponding to a direction in which the plurality of pixels pertaining to the different spaces is arranged is a horizontal direction in some cases. In addition, in the example illustrated in FIG. 4, the X-ray transmission image Xp is repeatedly captured a plurality of times, and 900 pixels corresponding to a plurality of pixels according to the number of times at which image capturing is repeated is acquired. Such a plurality of pixels is a plurality of pixels pertaining to different times of an X-ray transmission image. Hereinafter, a description may be given on the assumption that a time axis direction corresponding to a direction in which the plurality of pixels pertaining to the different times is arranged is a vertical direction in some cases. Therefore, in the example illustrated in FIG. 4, when pixels in the space axis direction and the time axis direction are combined, an X-ray transmission image Xa corresponding to 100 pixels× 900 pixels is acquired.

For example, a parameter pertaining to luminance values of a plurality of pixels of an X-ray transmission image refers to a statistical value of luminance values of the plurality of pixels of the X-ray transmission image. For example, the statistical value refers to a variation degree of the luminance values of the plurality of pixels. When a variation degree of luminance values set as an imaging condition by the controller 20 is larger than a predetermined value, the amplifier controller 18 sets a set amplification factor to low gain based on the imaging condition. On the other hand, when a variation degree of luminance values set as an imaging condition by the controller 20 is smaller than the predetermined value, the amplifier controller 18 sets the set amplification factor to high gain based on the imaging condition.

Figure 5:
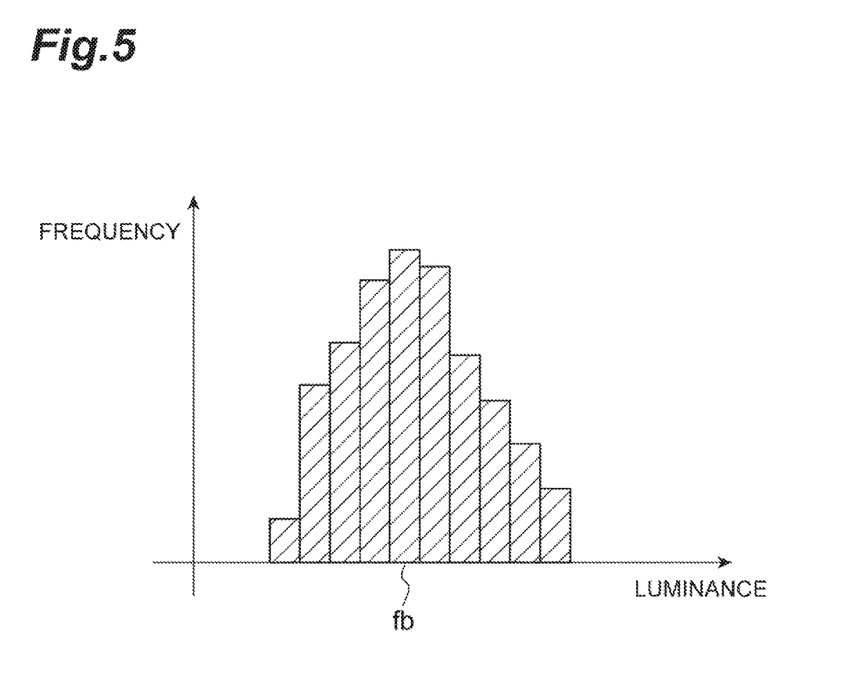
FIG. 5 is a diagram illustrating a variation of a luminance.

A variation degree of luminance values of a plurality of pixels is obtained based on a variation degree of luminance values of a plurality of pixels in the space axis direction. For example, in the example illustrated in FIG. 4, the variation degree of the luminance values of the plurality of pixels in the space axis direction may be obtained by obtaining an average luminance corresponding to an average value of luminance values in the time axis direction of pixels at the same position in the space axis direction, that is, by obtaining a time-based average luminance, and comparing respective average luminances at a plurality of pixel units in the space axis direction. A variation degree is obtained from a standard deviation, a difference between a maximum value and a minimum value, and the like. More specifically, a variation degree is obtained based on an error (%) with respect to a maximum frequency of an average luminance distribution. For example, as illustrated in FIG. 5, when a luminance fb is presumed to be a luminance value of a maximum frequency, that is, a luminance value corresponding to a greatest number of pixels in luminance values of a plurality of pixels, as a luminance value of a plurality of pixels in the space axis direction subjected to time averaging, an error of a luminance value with respect to the luminance fb is an error of a luminance value with respect to a maximum frequency. A variation degree is obtained based on an error (%) with respect to an average value or an intermediate value. That is, a variation degree may be obtained based on an error with respect to an average value or an intermediate value of a plurality of pixels in the space axis direction subjected to time averaging. Alternatively, a variation degree may be obtained based on a difference between a maximum value and a minimum value of a plurality of pixels in the space axis direction subjected to time averaging.

Further, a variation degree of luminance values of a plurality of pixels may be obtained by a variation degree of luminance values of a plurality of pixels in the time axis direction. In this case, the variation degree may be obtained by obtaining an average luminance corresponding to an average value of luminance values of pixels acquired at the same time, that is, by obtaining a space-based average luminance, and comparing respective average luminances at a plurality of pixel units in the time axis direction. A luminance value in the present embodiment may be an analog value or a digital value.

For example, setting of a set amplification factor based on an imaging condition by the amplifier controller 18 described above may be performed based on a table corresponding to a parameter of an imaging condition such as a variation degree of luminance values. That is, the amplifier controller 18 may store a table corresponding to a parameter of an imaging condition in advance, and determine whether to set high gain or low gain as a set amplification factor using the table. Alternatively, for example, setting of a set amplification factor based on an imaging condition by the amplifier controller 18 may be performed based on a threshold value corresponding to a parameter of an imaging condition such as a variation degree of luminance values. That is, the amplifier controller 18 may store a threshold value corresponding to a parameter of an imaging condition in advance, and determine whether to set high gain or low gain as a set amplification factor depending on whether the threshold value is exceeded.

Next, a description will be given of an image acquisition method using the image acquisition device 1. The present image acquisition method is an image acquisition method of acquiring an X-ray transmission image of the object F conveyed in the conveyance direction TD. In the present image acquisition method, first, an X-ray is output by the X-ray irradiator 50 corresponding to an X-ray source. In addition, the object F is conveyed in the conveyance direction TD by the belt conveyor 60. Subsequently, the X-ray penetrating the object F is converted into scintillation light by the scintillators 11a and 11b of the X-ray detection camera 10. Subsequently, scintillation light is detected by the line scan cameras 12a and 12b, and a detection signal is output. Then, the detection signal is amplified at a predetermined set amplification factor by the amplifiers 14a and 14b, and an amplified signal is output. At least before a step in which the amplified signal is output, one of high gain or low gain corresponding to an amplification factor lower than the high gain may be set as a set amplification factor based on a predetermined imaging condition by the amplifier controller 18. Finally, an X-ray transmission image is generated based on the amplified signal by the controller 20. The image acquisition method using the image acquisition device 1 has been described above.

Next, a description will be given of effect of the image acquisition device 1 according to the present embodiment described above.

In the image acquisition device 1 according to the present embodiment, a detection signal based on an X-ray penetrating the object F is amplified at a predetermined set amplification factor, and an X-ray transmission image is generated. In addition, one of high gain or low gain corresponding to an amplification factor lower than the first amplification factor is set as the set amplification factor based on a predetermined imaging condition. An amplification factor suitable to generate a clear X-ray transmission image is changed according to image condition, and thus a clear X-ray transmission image may be generated by selecting a set amplification factor depending on the imaging condition.

In addition, the line scan cameras 12a and 12b of the image acquisition device 1 have a plurality of line sensors arranged in a line in a direction interesting the conveyance direction TD. Scintillation light pertaining to the object F may be reliably detected by the plurality of line sensors.

Further, when an imaging condition is set as a parameter pertaining to luminance values of a plurality of pixels of an X-ray transmission image, the amplifier controller 18 may appropriately set a set amplification factor. More specifically, the parameter pertaining to the luminance values is a statistical value of luminance values of a plurality of pixels of an X-ray transmission image, and the statistical value is a variation degree of the luminance values of the plurality of pixels. When an X-ray transmission image of the object F conveyed by the belt conveyor 60 is acquired, the amount of X-ray entering the X-ray detection camera 10 greatly varies according to component included in the object F. For example, the amount of X-ray entering the X-ray detection camera 10 is small in a portion of the object F including a component that rarely transmits an X-ray. On the other hand, the amount of X-ray entering the X-ray detection camera 10 is large in a portion of the object F including a component that easily transmits an X-ray. A variation in luminance value of a plurality of pixels in an X-ray transmission image is generated due to such a difference in the amount of X-ray. When a variation degree of luminance values is great, an X-ray transmission image becomes clear by setting low gain. Therefore, when the amplifier controller 18 sets high gain or low gain using a variation of luminance values of a plurality of pixels as an imaging condition, it is possible to generate a clear X-ray transmission image, that is, an X-ray transmission image having an improved SN. When a variation degree of luminance values is small, the amplifier controller 18 may set high gain, thereby increasing a signal quantity and attempting a long life. A signal quantity is increased by setting change of the amplifier controller 18. Thus, an operation of increasing a tube voltage or a tube current corresponding to an output parameter of the X-ray irradiator 50 is not needed. It is understood that a life of the X-ray irradiator 50 is affected by a tube voltage or a tube current corresponding to an output parameter. When values thereof are increased, the life of the X-ray irradiator 50 is shortened. When a signal quantity is increased by setting change of gain by the amplifier controller 18, the signal quantity may be increased without increasing an output of the X-ray irradiator 50. Thus, the life of the X-ray irradiator 50 may be lengthened. Further, it is understood that lives of the line scan cameras 12a and 12b and the scintillators 11a and 11b are affected by an X-ray exposure dose. Therefore, when a signal quantity is increased by setting change of gain by the amplifier controller 18, the signal quantity may be increased without increasing an output parameter of the X-ray irradiator 50, and thus lives of the line scan cameras 12a and 12b and the scintillators 11a and 11b may be lengthened.

In addition, since an imaging condition is set based on an X-ray transmission image generated by the controller 20, the imaging condition may be easily set. Further, since the X-ray transmission image pertaining to setting of the imaging condition is generated under an environment in which high gain is set by the amplifier controller 18, a parameter pertaining to luminance values of a plurality of pixels of the X-ray transmission image is clear, and the parameter pertaining to the luminance values may be easily specified. In this way, an imaging condition may be more easily and appropriately set based on the X-ray transmission image.

In addition, a plurality of pixels of an X-ray transmission image is a plurality of pixels pertaining to different spaces of the X-ray transmission image. In this way, a set amplification factor may be appropriately set in consideration of a parameter of the plurality of pixels pertaining to the different spaces of the X-ray transmission image.

In addition, a plurality of pixels of an X-ray transmission image may be a plurality of pixels pertaining to different times of the X-ray transmission image. In this case, a set amplification factor may be appropriately set in consideration of a parameter of the plurality of pixels pertaining to the different times of the X-ray transmission image.

In addition, an imaging condition may be based on an output parameter of the X-ray irradiator 50, specifically, a tube voltage and a tube current pertaining to an X-ray output from the X-ray irradiator 50. When the tube voltage of the X-ray irradiator 50 is high, and the tube current of the X-ray irradiator 50 is low, luminance values of a plurality of pixels are prone to vary. For this reason, when the tube voltage which pertains to the X-ray and is set as the imaging condition by the controller 20 is higher than a predetermined value, and the tube current is lower than a predetermined value, the amplifier controller 18 sets a set amplification factor to low gain based on the imaging condition. On the other hand, when the tube voltage which pertains to the X-ray and is set as the imaging condition by the controller 20 is lower than a predetermined value, and the tube current is higher than a predetermined value, the amplifier controller 18 sets a set amplification factor to high gain based on the imaging condition. In this way, the set amplification factor may be appropriately set.

In addition, the amplifier controller 18 may have a table corresponding to a parameter of an imaging condition, and determine whether to set high gain or low gain as a set amplification factor using the table. In this way, a set amplification factor may be reliably and easily set.

In addition, the amplifier controller 18 may have a threshold value corresponding to a parameter of an imaging condition, and determine whether to set high gain or low gain as a set amplification factor depending on whether the threshold value is exceeded. In this way, a set amplification factor may be reliably and easily set.

The embodiment of the invention has been described above. However, the invention is not restricted to the above embodiment.

For example, a description has been given on the assumption that the X-ray detection camera is a dual-line X-ray camera. However, the invention is not limited thereto. The X-ray detection camera may be a single line X-ray camera, a dual energy X-ray camera, or a time delay integration (TDI) scan X-ray camera.

REFERENCE SIGNS LIST

1 . . . image acquisition device, 10 . . . X-ray detection camera, 11a, 11b . . . scintillator, 12a, 12b . . . line scan camera, 14a, 14b ... amplifier, 14x ... current-voltage converting amplifier, 14y ... voltage amplifier, 18 ... amplifier controller, 20 ... controller, 50 ... X-ray irradiator, F ... object, TD ... conveyance direction.

The invention claimed is:

1. A device for capturing a radiation image of an object conveyed in a conveyance direction, the device comprising:
a radiation source configured to output radiation;
a carrier device configured to convey the object in the conveyance direction;
a detector including a scintillator configured to convert radiation penetrating the object into scintillation light, a line scan camera configured to detect the scintillation light and output a detection signal, and an amplifier configured to amplify the detection signal at a predetermined set amplification factor and output an amplified signal;
an image generator configured to generate a radiation image based on the amplified signal; and
a controller configured to set one of a first amplification factor or a second amplification factor corresponding to an amplification factor lower than the first amplification factor as the set amplification factor based on a predetermined imaging condition parameter,
wherein the amplifier is connected in parallel to a first capacitance,
the amplifier being also connected in parallel to a second capacitance through a switch, and
the controller is configured to set the first amplification factor that is based on the first and second capacitances as the set amplification factor by closing the switch, and to set the second amplification factor that is based on the first capacitance as the set amplification factor by opening the switch.

2. The device according to claim 1, wherein the line scan camera has a plurality of line sensors arranged in a line in a direction intersecting the conveyance direction.

3. The device according to claim 1, wherein the imaging condition parameter corresponds to a parameter pertaining to luminance values of a plurality of pixels of the radiation image.

4. The device according to claim 1, wherein the imaging condition parameter is set based on the radiation image generated by the image generator.

5. The device according to claim 4, wherein the imaging condition parameter is set based on the radiation image generated by the image generator under an environment in which the set amplification factor is set to the first amplification factor.

6. The device according to claim 3, wherein the parameter pertaining to the luminance values is a statistical value of the luminance values of the plurality of pixels of the radiation image.

7. The device according to claim 6, wherein the statistical value is a variation degree of the luminance values of the plurality of pixels.

8. The device according to claim 3, wherein the plurality of pixels of the radiation image is a plurality of pixels pertaining to different spaces of the radiation image.

9. The device according to claim 3, wherein the plurality of pixels of the radiation image is a plurality of pixels pertaining to different times of the radiation image.

10. The device according to claim 1, wherein the imaging condition parameter is an output parameter of the radiation source.

11. The device according to claim 1, wherein the controller is configured to set the set amplification factor using a table corresponding to the parameter which is the imaging condition parameter.

12. The device according to claim 1, wherein the controller is configured to set the set amplification factor using a threshold value corresponding to the parameter which is the imaging condition parameter.

13. A method for capturing a radiation image of an object conveyed in a conveyance direction, the method comprising:
converting radiation penetrating the object into scintillation light;
detecting the scintillation light by a line scan camera;
outputting a detection signal corresponding to detected scintillation light;
setting one of a first amplification factor or a second amplification factor corresponding to an amplification factor lower than the first amplification factor as a set amplification factor based on a predetermined imaging condition parameter;
utilizing an amplifier to amplify the detection signal at the set amplification factor and output an amplified signal; and
generating a radiation image based on the amplified signal,
wherein the amplifier is connected in parallel to a first capacitance,
the amplifier being also connected in parallel to a second capacitance through a switch, and
the method further comprising setting the first amplification factor that is based on the first and second capacitances as the set amplification factor by closing the switch, and setting the second amplification factor that is based on the first capacitance as the set amplification factor by opening the switch.

14. The method according to claim 13, wherein the line scan camera has a plurality of line sensors arranged in a line in a direction intersecting the conveyance direction.

15. The method according to claim 13, wherein the imaging condition parameter corresponds to a parameter pertaining to luminance values of a plurality of pixels of the radiation image.

16. The method according to claim 13, wherein the imaging condition parameter is set based on the radiation image generated by the image generator.

17. The method according to claim 16 wherein the imaging condition parameter is set based on the radiation image generated by the image generator under an environment in which the set amplification factor is set to the first amplification factor.

18. The method according to claim 15, wherein the parameter pertaining to the luminance values is a statistical value of the luminance values of the plurality of pixels of the radiation image.

19. The method according to claim 18, wherein the statistical value is a variation degree of the luminance values of the plurality of pixels.

20. The method according to claim 15, wherein the plurality of pixels of the radiation image is a plurality of pixels pertaining to different spaces of the radiation image.

21. The method according to claim 15, wherein the plurality of pixels of the radiation image is a plurality of pixels pertaining to different times of the radiation image.

22. The method according to claim 1, wherein the imaging condition parameter is an output parameter of a radiation source.

23. The method according to claim 13, wherein the setting sets the set amplification factor using a table corresponding to the parameter which is the imaging condition parameter.

24. The method according to claim 13, wherein setting sets the set amplification factor using a threshold value corresponding to the parameter which is the imaging condition parameter.

* * * * *